United States Patent
Patil et al.

(10) Patent No.: US 9,078,597 B2
(45) Date of Patent: Jul. 14, 2015

(54) MOBILE X-RAY UNIT WITH INTEGRATED X-RAY SHIELD

(75) Inventors: Mahendra Madhukar Patil, Bangalore (IN); Arun A. Balan, Ermakulam (IN); Jijo Varghese, Bangalore (IN)

(73) Assignee: General Electric Company, Schenectady, NY (US)

( * ) Notice: Subject to any disclaimer, the term of this patent is extended or adjusted under 35 U.S.C. 154(b) by 463 days.

(21) Appl. No.: 13/439,953

(22) Filed: Apr. 5, 2012

(65) Prior Publication Data
US 2013/0266122 A1    Oct. 10, 2013

(51) Int. Cl.
*H05G 1/02* (2006.01)
*A61B 6/10* (2006.01)
*A61B 6/00* (2006.01)

(52) U.S. Cl.
CPC .............. *A61B 6/107* (2013.01); *A61B 6/4405* (2013.01); *A61B 6/4429* (2013.01); *Y10T 29/49826* (2015.01)

(58) Field of Classification Search
CPC ........ A61B 6/4405; A61B 6/10; A61B 6/107; G21F 3/00; G21F 7/02; G21F 7/03
USPC ...................... 378/198, 203; 250/515.1, 519.1
See application file for complete search history.

(56) References Cited

U.S. PATENT DOCUMENTS

| 4,387,468 | A | * | 6/1983 | Fenne et al. | 378/198 |
| 4,775,994 | A | * | 10/1988 | Kranvogel | 378/197 |
| 5,015,864 | A |   | 5/1991 | Maleki |  |
| 5,164,976 | A | * | 11/1992 | Scheid et al. | 378/146 |
| 7,465,947 | B2 | * | 12/2008 | Magram | 250/515.1 |
| 7,663,128 | B2 |   | 2/2010 | Arterson |  |

* cited by examiner

*Primary Examiner* — Jurie Yun
(74) *Attorney, Agent, or Firm* — Ziolkowski Patent Solutions Group, PC

(57) ABSTRACT

A mobile x-ray imaging unit with an integrated x-ray shield is disclosed. The mobile x-ray imaging unit includes a base, a column structure extending upwardly from the base, a horizontal arm mounted on the column structure, and an x-ray source positioned on the horizontal arm, with the x-ray source configured to generate x-ray radiation for acquisition of an x-ray image. The mobile x-ray imaging unit also includes an x-ray shield extending upwardly from the base on a side of the column structure opposite the x-ray source that is configured to attenuate x-ray radiation generated by the x-ray source, wherein at least a portion of the x-ray shield is formed of an optically transparent material and wherein the x-ray shield is sized so as to provide x-ray shielding to an operator when the operator is in a standing position.

21 Claims, 5 Drawing Sheets

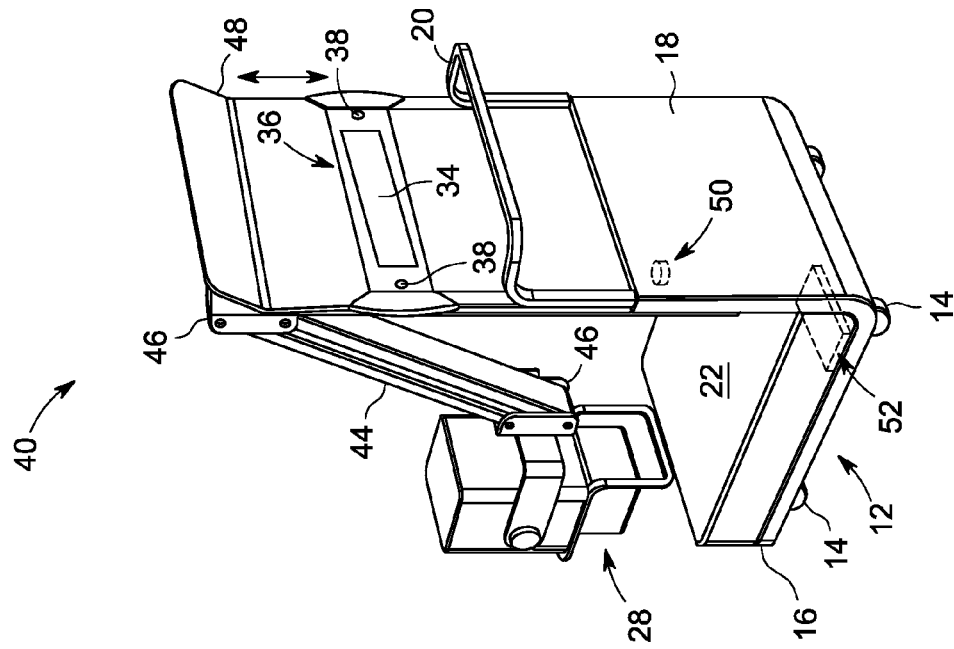
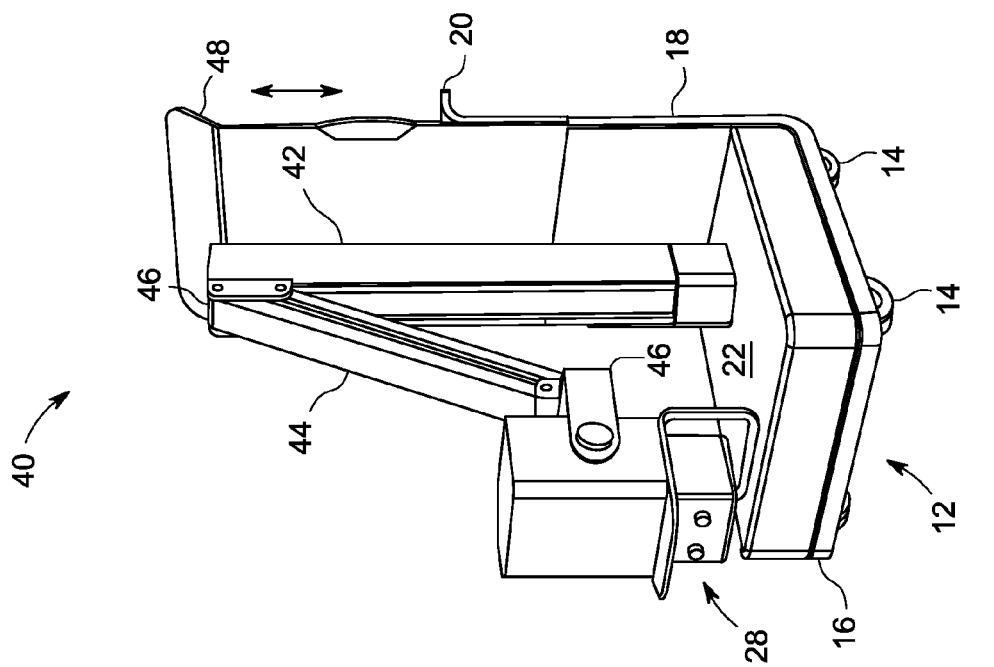

MOBILE X-RAY UNIT WITH INTEGRATED X-RAY SHIELD

BACKGROUND OF THE INVENTION

Embodiments of the invention relate generally to mobile x-ray imaging and, more particularly, to a mobile x-ray unit with an integrated x-ray shield and a method of manufacturing thereof.

Conventional mobile medical diagnostic-imaging systems, such as mobile digital x-ray imaging systems, are in widespread use by hospitals, trauma centers, and clinics. Mobile digital x-Ray imaging systems consist primarily of an x-ray generator and an x-ray tube mounted on a motorized chassis powered from a battery. The imaging is performed on imaging media of either chemical film or an electronic detector.

Mobile medical x-ray imaging systems are often used when a patient is unable to move to a fixed-based x-ray imaging system. To image the patient, a clinician moves the mobile medical x-ray imaging system to the patient, positions the tube on one side of the patient, places either a film screen cassette or an electronic detector on the other side of the patient, and images an exposure. For chemical film imaging, the clinician walks the film cassette to a film processor, develops the film and finally slips the finished film on a light box to make sure that the exposure was of diagnostic quality, considering, among other things, exposure technique and patient positioning. For electronic detectors, the electronic image data is stored on electronic media and physically transported to an electronic system that is capable of processing and/or displaying the image.

In operation of mobile medical x-ray imaging systems, it is recognized that the clinician or technician performing the scans must be shielded from the x-ray radiation generated by the system. Traditionally, clinicians are shielded from the x-ray radiation generated by the system by wearing a protective lead apron. However, it is recognized that there are numerous drawbacks associated with the wearing and use of such lead aprons. For example, protective lead aprons are typically very heavy and too inconvenient to repeatedly wear and take-off. Thus, there is a day-to-day discomfort and stress associated with the wearing and frequent changeovers (i.e., wearing/removal) of heavy lead aprons, and there are long-terms effects/injuries associated with the use of heavy lead aprons and its impact on the technician's well-being. Additionally, aprons are prone to come in contact with body fluids (e.g., blood) that can only be treated via manual washing, drying, and sanitizing, which is often a cumbersome task requiring staff to perform these tasks in a safe way (as the aprons are not suitable for machine washing). Furthermore, multiple technicians may sometimes be sharing the aprons and thus be vulnerable to the risks associated with improper hygienic conditions of the aprons.

In addition to user comfort and hygienic issues associated with the use of lead aprons, it is also recognized that such aprons may get damaged internally over time due to normal wear-and-tear and if they are not maintained well. If the technicians continue using these damaged aprons, they will potentially be exposed to harmful radiation, and thus meticulous and cumbersome apron tagging, along with strict observation of inspection and management protocols, must be implemented in order ensure that the lead aprons are in a usable condition. Even when the lead aprons are maintained in a proper condition, it is recognized that in some countries, owing to a lack of awareness and resources, technicians may be doing x-ray procedures without using adequate protection, as the mobile x-ray imaging system itself does not prevent misuse (e.g., operation of the system without wearing of an apron).

The use of lead aprons as a means for radiation shielding not only causes issues with respect to the health and safety of a wearer, but also causes issues with respect to the efficiency and accuracy of performing patient scans. That is, in the conventional method involving the technician to wear a protective lead apron, the technician will perform the adjustments and articulations of the x-ray tube, collimator, and detector on the mobile x-ray unit as needed with respect to the patient's body, then walk as far away from the unit as feasible (e.g., 12-15 feet away from the patient bed) before taking an exposure from a remote location via activation of the unit by a corded or cordless exposure switch. This movement by the technician to different locations increases the time required for the imaging operation and also prolongs the time for which the patient has to keep holding-on to a body posture along with x-ray cassette/detector, thus possibly causing discomfort for the patient. Furthermore, when taking the exposure from a remote location, it is difficult for the technician to monitor or verify if all the alignments and adjustments previously done were appropriate and have not been disturbed until the time of exposure. Thus, if the patient or the x-ray unit has moved without the technician noticing it while he/she walks to a remote location for taking the exposure, the image quality will be adversely affected.

Therefore, it would be desirable to design a mobile x-ray unit that provides x-ray radiation protection to a technician without the technician having to wear a protective lead apron. It would also be desirable for such a mobile x-ray unit to enable the technician to take x-ray exposures by staying in close proximity with the patient and the mobile x-ray unit itself, while constantly assuring and communicating with the patient during the procedure.

BRIEF DESCRIPTION OF THE INVENTION

Embodiments of the invention overcome the aforementioned drawbacks by providing a mobile x-ray unit with an integrated x-ray shield. The x-ray shield on the mobile x-ray unit provides x-ray radiation protection to a technician and negates the need for the technician having to wear a protective lead apron.

In accordance with one aspect of the invention, a mobile x-ray imaging unit includes a base, a column structure extending upwardly from the base, a horizontal arm mounted on the column structure, an x-ray source positioned on the horizontal arm and configured to generate x-ray radiation for acquisition of an x-ray image, and an x-ray shield extending upwardly from the base on a side of the column structure opposite the x-ray source and being configured to attenuate x-ray radiation generated by the x-ray source, wherein at least a portion of the x-ray shield is formed of an optically transparent material and wherein the x-ray shield is sized so as to provide x-ray shielding to an operator when the operator is in a standing position.

In accordance with another aspect of the invention, a mobile x-ray imaging unit includes a wheeled base comprising a bottom plane and a back plane, a column structure extending upwardly from the bottom plane of the base, a horizontal arm mounted on the column structure, an x-ray source positioned on the horizontal arm and configured to generate x-ray radiation to accommodate acquisition of an x-ray image, and an x-ray shield extending upwardly from the bottom plane of the base and up to a height that is greater than a height of the back plane, with the x-ray shield being configured to shield an operator from x-ray radiation generated by the x-ray source during operation thereof and being constructed, at least in part, of an optically transparent material to enable the operator to view a subject being imaged.

In accordance with yet another aspect of the invention, a method of manufacturing a mobile x-ray imaging unit includes providing a base, affixing a vertically oriented column structure to the base, and mounting a horizontal arm onto the column structure, with the horizontal arm including an x-ray source attached thereto on an end distal from the column structure that is configured to generate x-ray radiation for acquisition of an x-ray image. The method also includes positioning a vertically oriented x-ray shield on the base on a side of the column structure opposite the x-ray source, with the x-ray shield being formed at least in part of an optically transparent material configured to attenuate x-ray radiation generated by the x-ray source, so as to shield an operator from the x-ray radiation.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings:

FIGS. 5 and 6 are perspective views of the mobile x-ray imaging unit of FIGS. 3 and 4 with the x-ray shield moved to a vertically collapsed position.

DETAILED DESCRIPTION OF THE PREFERRED EMBODIMENT

Embodiments of the invention are directed to a mobile x-ray imaging unit having an integrated x-ray shield. The x-ray shield has at least a partial section that is optically transparent so as to enable an x-ray technician to observe and communicate with the patient being scanned during preparation and exposure from a location behind the said x-ray shield. The transparent section of the integral x-ray shield is formed of a material having a thickness sufficient to attenuate stray x-ray radiation. The form of the generally vertically deployed x-ray shield is sufficient to cover the standing height and breadth of an adult technician while also leaving reasonable margin to accommodate various standing postures of the technician behind it during exposure.

Figure 1:
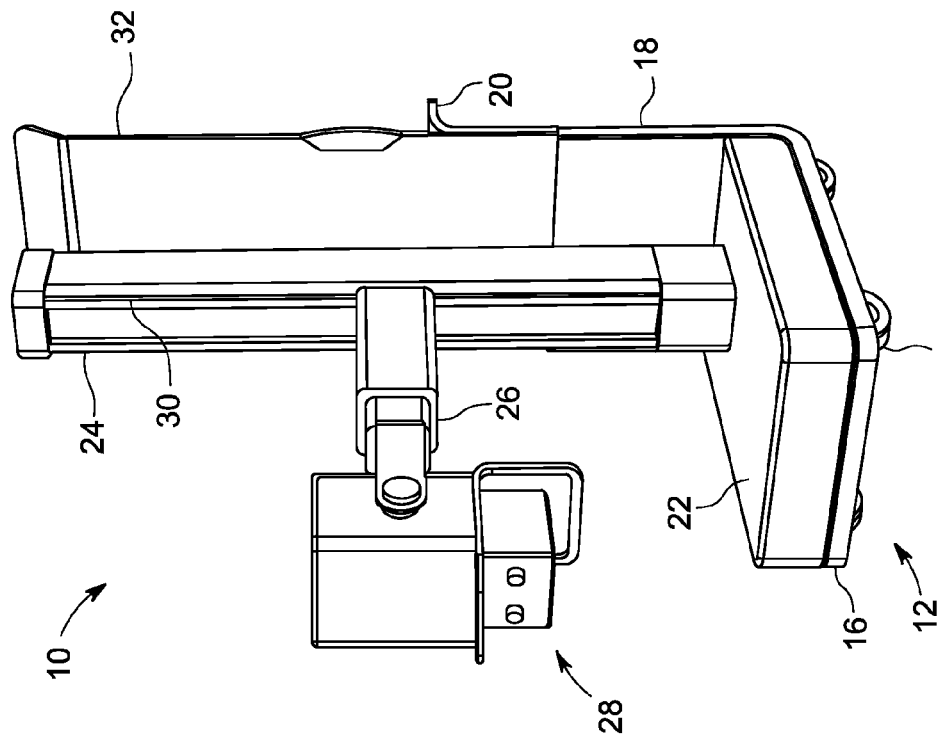
FIGS. 1 and 2 are perspective views of a mobile x-ray imaging unit with an integrated x-ray shield according to an embodiment of the invention.
Figure 2:
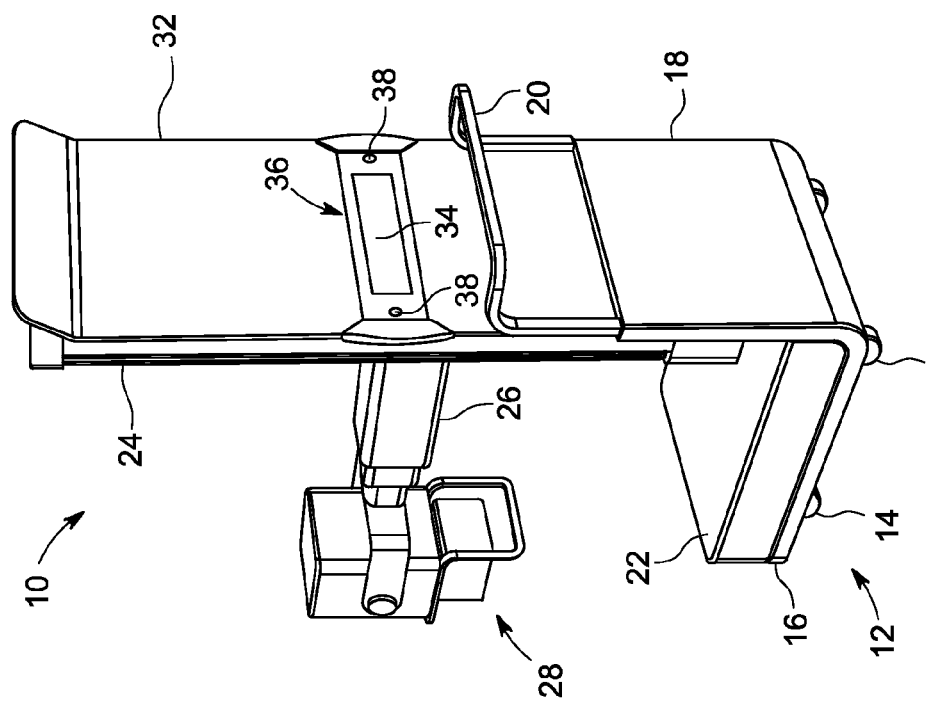

Referring to FIGS. 1 AND 2, a mobile x-ray imaging unit 10 is shown according to an embodiment of the invention. The mobile x-ray imaging unit 10 includes a base 12 having wheels 14 thereon that provide mobility to the system 10. As shown in FIGS. 1 AND 2, the base 12 is constructed as an L-shaped base that includes a bottom plane 16 and a back plane 18 that extends upwardly from the bottom plane 16 along a back side of the mobile x-ray imaging unit 10. The back plane 18 includes a handle 20 thereon that enables an x-ray technician to maneuver the imaging unit 10 and move it from location to location. The base 12 also includes a housing 22 mounted on bottom plane 16 that is configured to enclose electrical hardware (not shown) associated with operation of the mobile x-ray imaging unit 10. For example, electrical hardware associated with x-ray image acquisition and processing of the acquired x-ray images may be housed within housing 22.

Affixed to base 12 is a vertically oriented column structure 24 that extends upward from the base 12. A horizontally oriented telescopic arm 26 is mounted on the column structure 24, with the telescopic arm 26 having an x-ray source 28 that is mounted a distal end thereof. The telescopic arm 26 is mounted on the column structure 24 by way of a track 30 formed on the column structure 24, so as to be slidable there along in a vertical direction. The telescopic arm 26 can thus be translated up or down along the track 30 of column structure 24 so as to vary a height of the x-ray source 28. The telescopic arm 26 can also be extended inwardly and outwardly to vary a position of the x-ray source 28 relative to the column structure 24. Based on the horizontal and vertical translation of the x-ray source 28 provided by the telescopic arm 26 and the mounting thereof on the column structure 24, the x-ray source 28 can thus be positioned as desired over an area of concern on a patient for acquisition of an x-ray image of the patient.

As shown in FIGS. 1 AND 2, an integrated x-ray shield 32 is provided on mobile x-ray imaging unit 10 that is configured to shield the x-ray technician from radiation emitted during scanning of a patient. According to one embodiment, the x-ray shield 32 is affixed to the column structure 24 and back plane 18 of base 12. The x-ray shield 32 is constructed so as to be generally vertically deployed and to have a size and dimensions that are sufficient to cover the standing height and breadth of an adult technician, while also leaving reasonable leeway to accommodate various standing postures of the technician behind it during exposure. Thus, according to the embodiment of mobile x-ray imaging unit 10 illustrated in FIGS. 1 AND 2, the x-ray shield 32 will have a height of at least six feet and a width of at least two feet, for example.

The x-ray shield 32 is further constructed such that at least a partial section of the shield is optically transparent, so as to enable the x-ray technician to observe and communicate with the patient being scanned during preparation and exposure from a location behind the x-ray shield 32. Accordingly, the technician can take x-ray exposures by staying in close proximity to the patient and the mobile x-ray imaging unit 10 to enable observation of the patient's body posture/movements, x-ray source position, and collimator lighting, while also enabling communication between the technician and the patient during the procedure via line-of-sight and communication through hand gestures, direct eye contact, and spoken instructions. In order to provide appropriate x-ray shielding to the technician, the transparent section of the integral x-ray shield 32 is formed of a material that effectively attenuates stray x-ray radiation generated during a scan of the patient. Thus, according to embodiments of the invention, the x-ray shield 32 may be formed of leaded glass (ceramic), leaded acrylic (polymeric/plastic), or other suitable material of equivalent Pb thickness that attenuates the stray x-ray radiation.

As further shown in FIGS. 1 AND 2, a display 34 and control panel 36 are included on mobile x-ray imaging unit 10 that are used by the technician in connection with a scanning operation of the patient. The display 34 and control panel 36 are mounted on top of the back plane 18 and secured to x-ray shield 32, at a height that is convenient for the technician to view and operate/manipulate with his hands. In operation, the control panel 36 functions to control operation of various components of the system, such as controlling movement of telescopic arm 26 (both horizontally and vertically) and the emitting of x-rays by x-ray source 28.

According to an exemplary embodiment, control panel 36 includes a pair of exposure switches 38 arranged proximate to the left and right side vertical edges of the x-ray shield 32. In operation, the technician initiates an exposure via x-ray source 28 by simultaneously pressing/activating both of the exposure switches 38. The activation of x-ray source 28 by pressing both exposure switches 38 ensures that the technician is always in a secure location, centered behind the x-ray shield 32 while taking the exposure, thereby removing any possibilities of an unsafe/negligent use of the imaging unit 10 by an x-ray technician. A fool-proof arrangement for the technicians to protect themselves during x-ray procedures is thus provided.

Referring now to FIGS. 3-6, a mobile digital x-ray imaging unit 40 is shown according to another embodiment of the invention. The mobile x-ray imaging unit 40 includes a base 12 having wheels 14 thereon that provide mobility to the system 10. The base 12 is constructed as an L-shaped base that includes a bottom plane 16 and a back plane 18 that extends upwardly from the bottom plane 16 along a back side of the mobile x-ray imaging unit 40. The back plane 18 includes a handle 20 thereon that enables an x-ray technician to maneuver the imaging unit 40 and move it from location to location. The base 12 also includes a housing 22 mounted on bottom plane 16 that is configured to enclose electrical hardware (not shown) associated with operation of the mobile x-ray imaging unit 40. For example, electrical hardware associated with x-ray image acquisition and processing of the acquired x-ray images may be housed within housing 22.

Affixed to base 12 is a vertically oriented column structure 42 that extends upward from the base 12. A hinged arm 44 supporting an x-ray source 28 is mounted on the column structure 42 and includes hinges 46 that enable the arm 44 to be moved both horizontally and vertically to accommodate positioning of the x-ray source 28 relative to a patient as desired by a technician. The hinged arm 44 thus provides for positioning of the x-ray source 28 as desired over an area of concern on a patient for acquisition of an x-ray image of the patient.

Also included on mobile x-ray imaging unit 40 is an integrated x-ray shield 48 configured to shield the x-ray technician from radiation emitted during scanning of a patient. According to one embodiment, the x-ray shield 48 is affixed to the column structure 42 and back plane 18 of base 12. The x-ray shield 48 is constructed such that at least a partial section of the shield is optically transparent, so as to enable the x-ray technician to observe and communicate with the patient being scanned during preparation and exposure from a location behind the x-ray shield 48, with the shield having a size and dimensions that are sufficient to cover the height and breadth of an adult technician. The transparent section of the integral x-ray shield 48 is formed of a material that effectively attenuates stray x-ray radiation generated during a scan of the patient. Thus, according to embodiments of the invention, the x-ray shield 48 may be formed of leaded glass (ceramic), leaded acrylic (polymeric/plastic), or other suitable material of equivalent Pb thickness that attenuates the stray x-ray radiation.

Figure 4:
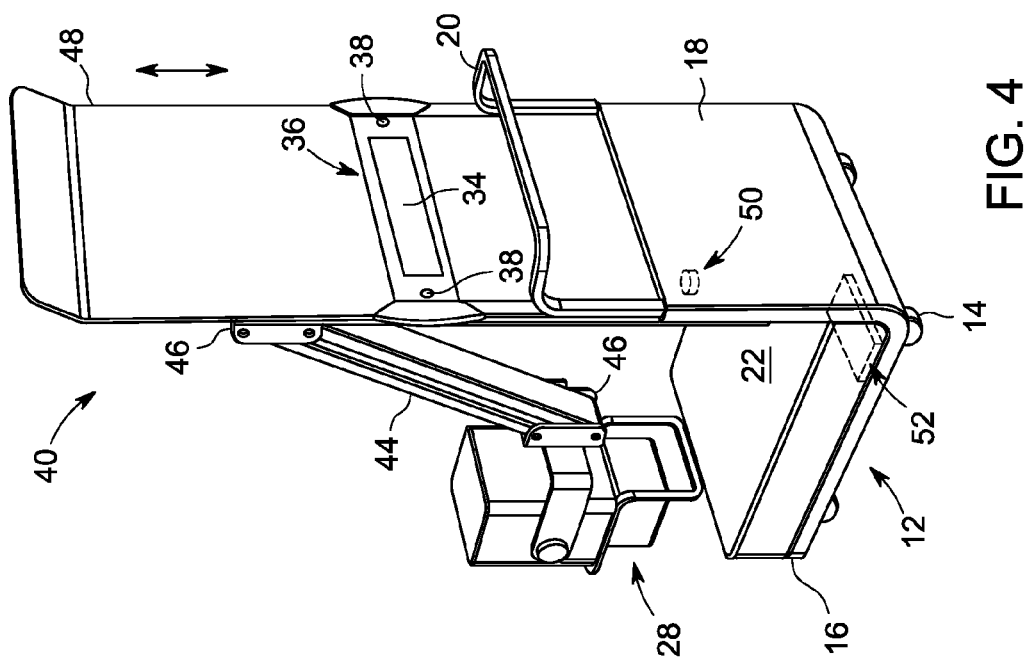
FIGS. 3 and 4 are perspective views of a mobile x-ray imaging unit with an integrated x-ray shield moved to a vertically extended position according to another embodiment of the invention.
Figure 3:
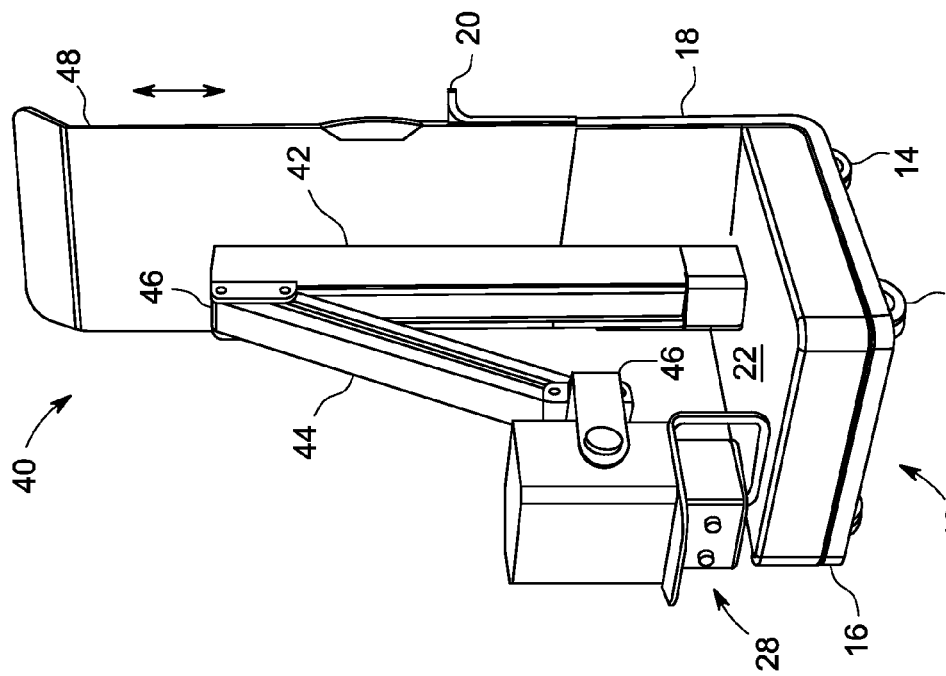

As shown in FIGS. 3-6, the x-ray shield 48 is configured as a telescopically collapsing/expanding member that facilitates rapid full deployment and folding back of the shield 48 during and after use, respectively, as desired by a technician. The extendable x-ray shield 48 is configured to slide in a vertical direction between an extended position and a collapsed position, such that a height of the x-ray shield 48 can be varied. As shown in FIGS. 3 and 4, the x-ray shield 48 is in an extended/expanded position, such as would be desired when performing an x-ray scan on a patient. In the extended position, the x-ray shield 48 has a height sufficient to cover the standing height of an adult technician, while also leaving reasonable leeway to accommodate various standing postures of the technician behind it during exposure. As shown in FIGS. 5 and 6, the x-ray shield 48 is in a collapsed or retracted position, such as would be desired when the mobile x-ray imaging unit 40 is not in use, so as to facilitate moving of the system and storage thereof in small areas, such as under staircases and under wall-mounted cabinets, for example.

As further shown in FIGS. 3-6, a display 34 and control panel 36 are included on mobile x-ray imaging unit 40 that are used by the technician in connection with a scanning operation of the patient. The display 34 and control panel 36 are mounted on top of the back plane 18 and secured to x-ray shield 48, at a height that is convenient for the technician to view and operate/manipulate with his hands. In operation, the control panel 36 functions to control operation of various components of the system, such as controlling movement of telescopic arm 26 (both horizontally and vertically) and the emitting of x-rays by x-ray source 28.

According to an exemplary embodiment, control panel 36 includes a pair of exposure switches 38 arranged proximate to the left and right side vertical edges of the x-ray shield 48. In operation, the technician initiates an exposure via x-ray source 28 by simultaneously pressing/activating both of the exposure switches 38. The activation of x-ray source 28 by pressing both exposure switches 38 ensures that the technician is always in a secure location, centered behind the x-ray shield 48 while taking the exposure, thereby removing any possibilities of an unsafe/negligent use of the imaging unit 10 by an x-ray technician. A fool-proof arrangement for the technicians to protect themselves during x-ray procedures is thus provided.

According to an exemplary embodiment, where in the x-ray shield 48 is configured as a telescopically collapsing/expanding member, the mobile x-ray unit also has a transducer 50 that detects the collapsed and extended states of the x-ray shield 48 and a controller 52 configured to enable operation of the x-ray source 28 only when the x-ray shield 48 is in its extended state, thus making the operation of the mobile x-ray imaging unit 40 adequately fool-proof. The transducer 50 provided may be one of a contact switch (micro-switch/limit-switch), a potentiometer, an optical switch/encoder, a magnetic switch/encoder, or similar device.

Figure 8:
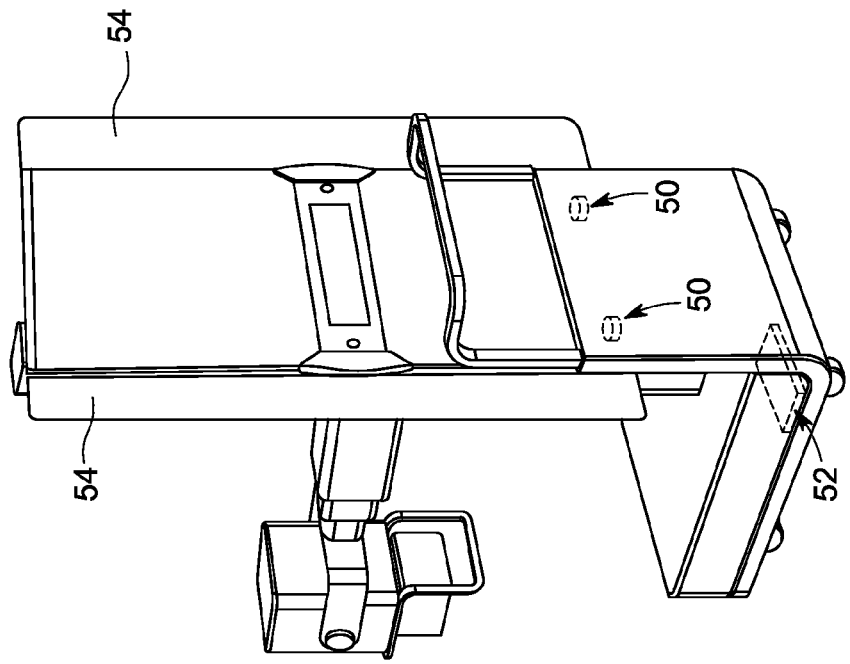
FIGS. 7 and 8 are perspective views of a mobile x-ray imaging unit with an integrated x-ray shield moved to horizontally extended and retracted positions according to another embodiment of the invention.
Figure 7:
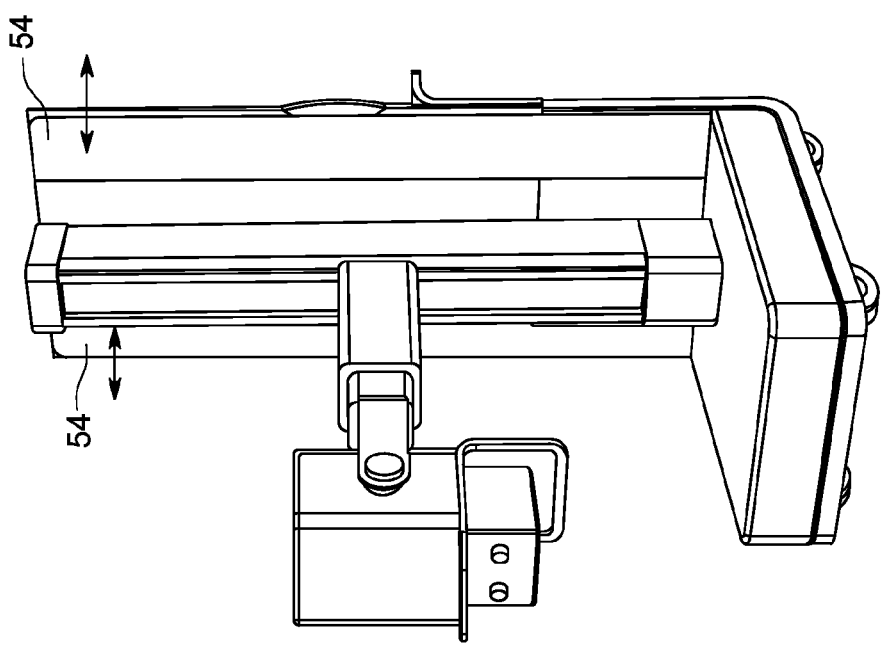
Figure 10:
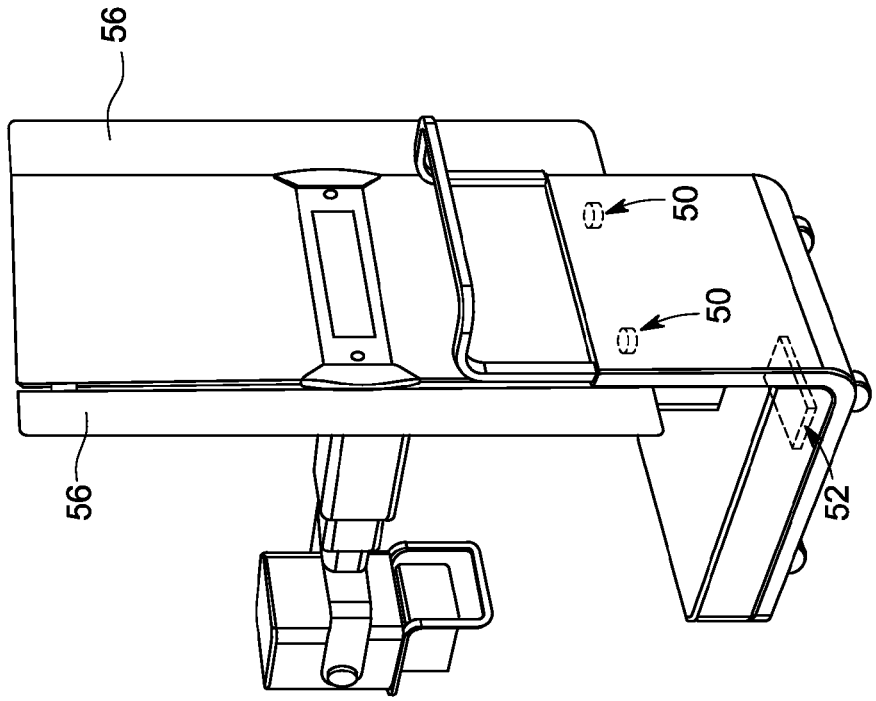
FIGS. 9 and 10 are perspective views of a mobile x-ray imaging unit with an integrated x-ray shield moved to horizontally extended and retracted positions according to another embodiment of the invention.
Figure 9:
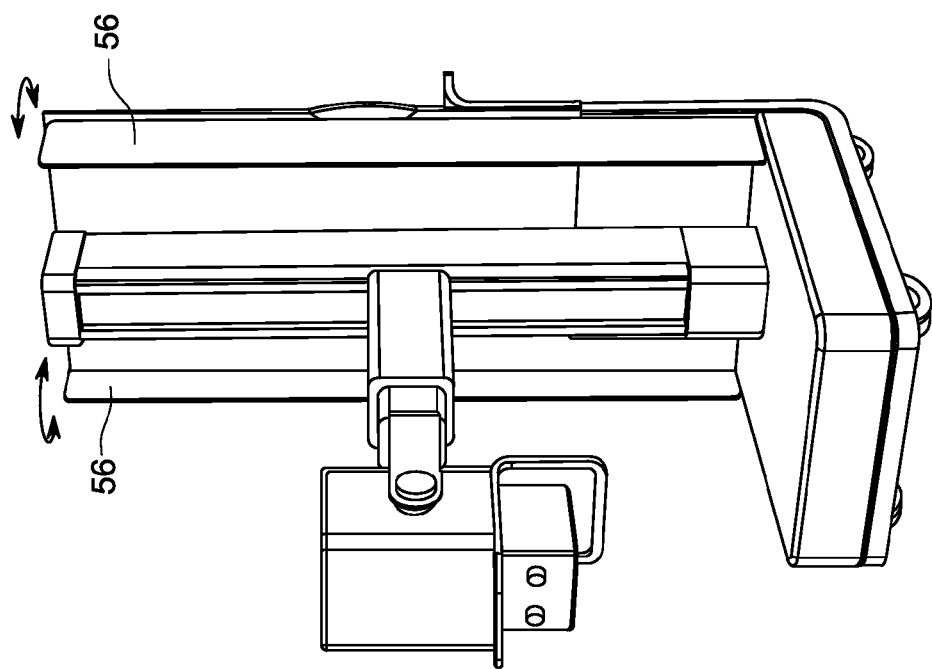

Referring now to FIGS. 7-10, additional embodiments of mobile digital x-ray imaging unit 10 are shown that incorporate a collapsing/expanding x-ray shield member that increases coverage for a technician in a horizontal direction/dimension. In the embodiments of FIGS. 7-10, the x-ray shield is configured as a collapsing/expanding member that facilitates rapid full deployment and folding or sliding back of the shield during and after use, respectively, as desired by a technician. In the embodiment of FIGS. 7-8, an extendable x-ray shield 54 is provided that is configured to slide in and out between an extended position and a collapsed position, such that a width of the x-ray shield 54 can be varied. In FIGS. 9-10, an extendable x-ray shield 56 is provided that is configured to hinge inward and outward in a horizontal direction between an extended position and a collapsed position, such that a width of the x-ray shield 56 can be varied. As shown in FIGS. 8 and 10, the x-ray shield 54, 56 is in an extended position, such as would be desired when performing an x-ray scan on a patient. In the extended position, the x-ray shield 54, 56 has a width sufficient to cover the standing dimensions of an adult technician, while also leaving reasonable leeway to accommodate various standing postures of the technician behind it during exposure. As shown in FIGS. 7 and 9, the x-ray shield 54, 56 is in a collapsed or retracted position. The collapsed or retracted position of x-ray shield 54, 56 reduces the footprint of the mobile x-ray imaging unit 10 and helps in maneuvering it in compact spaces, such as in an inter-bed space between two adjacent beds or in an elevator/lift in hospital facilities, while also saving some space needed to park/store the unit in hospital facilities.

As shown in FIGS. 8 and 10, mobile x-ray unit 10 includes transducers 50 that detect the collapsed and extended states of the x-ray shield 54, 56 and a controller 52 configured to enable operation of the x-ray source 28 only when the x-ray shield 54, 56 is in its extended state, thus making the operation of the mobile x-ray imaging unit 10 adequately foolproof. The transducers 50 provided may be one of a contact switch (micro-switch/limit-switch), a potentiometer, an optical switch/encoder, a magnetic switch/encoder, or similar device.

It is recognized that the embodiments of the invention set forth above are broadly applicable to both analog and digital mobile x-ray imaging units in many applications and scenarios. That is, it will be appreciated by those skilled in the art that embodiments of the invention are applicable not only to mobile x-ray units that employ digital detectors, but are equally applicable for use with analog units that employ film screen cassettes rather than an electronic detector.

Beneficially, embodiments of the invention thus provide x-ray radiation protection to a technician and negate the need for the technician having to wear a protective lead apron, thereby eliminating the drawbacks associated with the use of such aprons. Embodiments of the invention also benefit health administrators by eliminating the need for periodic fluoroscopic inspection of lead shielding aprons, identification and record keeping of inspected/in-service aprons for regulatory audits, cumbersome protocols for safe disposal of damaged lead aprons, and the recurring cost of replacing the damaged aprons and liabilities towards the long term health of the technicians. Embodiments of the invention also enhance patient throughput productivity due to shortened and more efficient workflow and higher employee satisfaction. Furthermore, embodiments of the invention are broadly applicable to both analog and digital mobile x-ray imaging units.

Therefore, according to one embodiment of the invention, a mobile x-ray imaging unit includes a base, a column structure extending upwardly from the base, a horizontal arm mounted on the column structure, an x-ray source positioned on the horizontal arm and configured to generate x-ray radiation for acquisition of an x-ray image, and an x-ray shield extending upwardly from the base on a side of the column structure opposite the x-ray source and being configured to attenuate x-ray radiation generated by the x-ray source, wherein at least a portion of the x-ray shield is formed of an optically transparent material and wherein the x-ray shield is sized so as to provide x-ray shielding to an operator when the operator is in a standing position.

According to another embodiment of the invention, a mobile x-ray imaging unit includes a wheeled base comprising a bottom plane and a back plane, a column structure extending upwardly from the bottom plane of the base, a horizontal arm mounted on the column structure, an x-ray source positioned on the horizontal arm and configured to generate x-ray radiation to accommodate acquisition of an x-ray image, and an x-ray shield extending upwardly from the bottom plane of the base and up to a height that is greater than a height of the back plane, with the x-ray shield being configured to shield an operator from x-ray radiation generated by the x-ray source during operation thereof and being constructed, at least in part, of an optically transparent material to enable the operator to view a subject being imaged.

According to yet another embodiment of the invention, a method of manufacturing a mobile x-ray imaging unit includes providing a base, affixing a vertically oriented column structure to the base, and mounting a horizontal arm onto the column structure, with the horizontal arm including an x-ray source attached thereto on an end distal from the column structure that is configured to generate x-ray radiation for acquisition of an x-ray image. The method also includes positioning a vertically oriented x-ray shield on the base on a side of the column structure opposite the x-ray source, with the x-ray shield being formed at least in part of an optically transparent material configured to attenuate x-ray radiation generated by the x-ray source, so as to shield an operator from the x-ray radiation.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A mobile x-ray imaging unit comprising:
   a base;
   a column structure extending upwardly from the base;
   a horizontal arm mounted on the column structure;
   an x-ray source positioned on the horizontal arm and configured to generate x-ray radiation for acquisition of an x-ray image;
   an x-ray shield extending upwardly from the base on a side of the column structure opposite the x-ray source and being configured to attenuate x-ray radiation generated by the x-ray source, wherein at least a portion of the x-ray shield is formed of an optically transparent material and wherein the x-ray shield is sized so as to provide x-ray shielding to an operator when the operator is in a standing position; and
   a display and a control panel configured to control operation and positioning of the x-ray source, the control panel comprising a pair of exposure switches configured to control operation of the x-ray source;
   wherein the generation of x-ray radiation by the x-ray source is initiated when the pair of exposure switches is simultaneously pressed; and
   wherein the pair of exposure switches are arranged proximate to left and right side vertical edges of the x-ray shield, respectively, such that a technician is centered behind the x-ray shield when simultaneously pressing the pair of exposure switches.

2. The mobile x-ray imaging unit of claim 1 wherein the optically transparent material comprises one of leaded glass and a leaded acrylic material.

3. The mobile x-ray imaging unit of claim 1 wherein the column structure includes a vertically oriented track formed thereon.

4. The mobile x-ray imaging unit of claim 3 wherein the horizontal arm comprises a telescopic arm configured to extend in a horizontal direction and slide along the track on the column structure in a vertical direction, so as to provide for positioning of the x-ray source.

5. The mobile x-ray imaging unit of claim 1 wherein the horizontal arm comprises a hinged arm attached to an upper end of the column structure, the hinged arm configured to enable movement of the x-ray source both horizontally and vertically to provide for positioning of the x-ray source.

6. The mobile x-ray imaging unit of claim 1 wherein the x-ray shield comprises a telescopic shield that is expandable in a vertical direction between an extended position and a collapsed position, such that a height of the x-ray shield can be varied.

7. The mobile x-ray imaging unit of claim 6 further comprising:
    at least one transducer configured to detect the extended position of the x-ray shield; and
    a controller configured to enable operation of the x-ray source only when the x-ray shield is in its extended position.

8. The mobile x-ray imaging unit of claim 1 wherein the x-ray shield comprises a shield that is expandable in a horizontal direction between an extended position and a collapsed position, such that a width of the x-ray shield can be varied.

9. The mobile x-ray imaging unit of claim 8 further comprising:
    at least one transducer configured to detect the extended position of the x-ray shield; and
    a controller configured to enable operation of the x-ray source only when the x-ray shield is in its extended position.

10. A mobile x-ray imaging unit comprising:
    a wheeled base comprising a bottom plane and a back plane;
    a column structure extending upwardly from the bottom plane of the base;
    a horizontal arm mounted on the column structure;
    an x-ray source positioned on the horizontal arm, the x-ray source configured to generate x-ray radiation to accommodate acquisition of an x-ray image;
    an x-ray shield extending upwardly from the bottom plane of the base and up to a height that is greater than a height of the back plane, the x-ray shield being configured to shield an operator from x-ray radiation generated by the x-ray source during operation thereof and being constructed, at least in part, of an optically transparent material to enable the operator to view a subject being imaged; and
    a control panel positioned adjacent a top edge of the back plane of the base and on a side of the x-ray shield opposite the column structure, the control panel comprising a pair of exposure switches configured to control operation of the x-ray source;
    wherein the pair of exposure switches are arranged proximate to left and right side vertical edges of the x-ray shield, respectively, and wherein generation of x-ray radiation by the x-ray source is initiated when the pair of exposure switches is simultaneously pressed.

11. The mobile x-ray imaging unit of claim 10 wherein the optically transparent material is configured to attenuate x-ray radiation generated by the x-ray source.

12. The mobile x-ray imaging unit of claim 11 wherein the optically transparent material comprises one of leaded glass and a leaded acrylic material.

13. The mobile x-ray imaging unit of claim 12 wherein the horizontal arm comprises a telescopic arm extendable in a horizontal direction, the telescopic arm configured to translate along the column structure in a vertical direction.

14. The mobile x-ray imaging unit of claim 10 wherein the horizontal arm comprises a hinged arm attached to an upper end of the column structure, the hinged arm configured to enable movement of the x-ray source in horizontal and vertical directions.

15. The mobile x-ray imaging unit of claim 10 wherein the x-ray shield comprises an extendable x-ray shield configured to slide in a vertical direction between an extended position and a collapsed position, such that a height of the x-ray shield can be varied.

16. The mobile x-ray imaging unit of claim 15 further comprising:
    at least one transducer configured to detect the extended position of the x-ray shield; and
    a controller configured to enable operation of the x-ray source only when the said x-ray shield is in its extended position.

17. The mobile x-ray imaging unit of claim 10 wherein the x-ray shield comprises a shield that is expandable in a horizontal direction between an extended position and a collapsed position, such that a width of the x-ray shield can be varied.

18. The mobile x-ray imaging unit of claim 17 further comprising:
    at least one transducer configured to detect the extended position of the x-ray shield; and
    a controller configured to enable operation of the x-ray source only when the said x-ray shield is in its extended position.

19. A method of manufacturing a mobile x-ray imaging unit, the method comprising:
    providing a base;
    affixing a vertically oriented column structure to the base;
    mounting a horizontal arm onto the column structure, the horizontal arm including an x-ray source attached thereto on an end distal from the column structure that is configured to generate x-ray radiation for acquisition of an x-ray image;
    positioning a vertically oriented x-ray shield on the base on a side of the column structure opposite the x-ray source, the x-ray shield being formed at least in part of an optically transparent material configured to attenuate x-ray radiation generated by the x-ray source, so as to shield an operator from the x-ray radiation; and
    affixing a control panel onto a back surface of the x-ray shield, the control panel comprising a pair of exposure switches configured to control operation of the x-ray source, with the pair of exposure switches being positioned proximate to left and right side vertical edges of the x-ray shield, respectively, such that the operator is centered behind the x-ray shield when simultaneously pressing the pair of exposure switches.

20. The method of claim 19 wherein the vertically oriented x-ray shield is configured to be extendable in at least one of a vertical direction and a horizontal direction; and
    wherein the method further comprises:
        providing at least one transducer configured to detect when the x-ray shield is in an extended state; and providing a controller configured to enable operation of the x-ray source only when the x-ray shield is in the extended state, so as to shield the operator from the x-ray radiation.

21. A mobile x-ray imaging unit comprising:

a base;

a column structure extending upwardly from the base;

a horizontal arm mounted on the column structure;

an x-ray source positioned on the horizontal arm and configured to generate x-ray radiation for acquisition of an x-ray image;

an x-ray shield extending upwardly from the base on a side of the column structure opposite the x-ray source and being configured to attenuate x-ray radiation generated by the x-ray source, wherein at least a portion of the x-ray shield is formed of an optically transparent material and wherein the x-ray shield is sized so as to provide x-ray shielding to an operator when the operator is in a standing position, and wherein the x-ray shield comprises a telescopic shield that is expandable in a vertical direction between an extended position and a collapsed position, such that a height of the x-ray shield can be varied;

at least one transducer configured to detect the extended position of the x-ray shield; and a controller configured to enable operation of the x-ray source only when the x-ray shield is in its extended position.

* * * * *